United States Patent [19]
Schwartz et al.

[11] Patent Number: 5,840,295
[45] Date of Patent: Nov. 24, 1998

[54] NERVE-DERIVED TRANSGLUTAMINASE ENZYME

[75] Inventors: Michal Schwartz, Rehovot; Shoshana Eitan, Tel-Aviv, both of Israel

[73] Assignee: Yeda Research and Development Co., Ltd., Rehovot, Israel

[21] Appl. No.: 467,202

[22] Filed: Jun. 7, 1995

Related U.S. Application Data

[60] Division of Ser. No. 99,759, Jul. 30, 1993, Pat. No. 5,514,565, which is a continuation-in-part of Ser. No. 840,783, Feb. 24, 1992, abandoned, which is a continuation-in-part of Ser. No. 573,580, Aug. 27, 1990, abandoned.

[30] Foreign Application Priority Data

| Jul. 30, 1992 | [IL] | Israel | 102686 |
| Oct. 20, 1992 | [IL] | Israel | 103469 |
| May 19, 1993 | [IL] | Israel | 105752 |

[51] Int. Cl.⁶ .................................. A61K 38/45
[52] U.S. Cl. .................. 424/94.5; 435/68.1; 435/193
[58] Field of Search .................... 435/68.1, 193; 424/94.5

[56] References Cited

U.S. PATENT DOCUMENTS 5,514,573  5/1996  Yasueda et al. .................. 435/240.2
5,514,579  5/1996  O'Hara et al. .................... 435/240.2

*Primary Examiner*—Jean C. Witz
*Attorney, Agent, or Firm*—Keck, Mahin & Cate

[57] ABSTRACT

The invention provides a new nerve-derived transglutaminase enzyme that converts immune-derived IL-2 to dimeric IL-2 having oligodendrocyte cytotoxic activity. Both the nerve-derived transglutaminase and the dimeric mammalian, e.g. human, IL-2, are for use as active ingredients in pharmaceutical compositions for inducing and facilitating regeneration of injured nerves of the central nervous system in mammals.

13 Claims, 15 Drawing Sheets

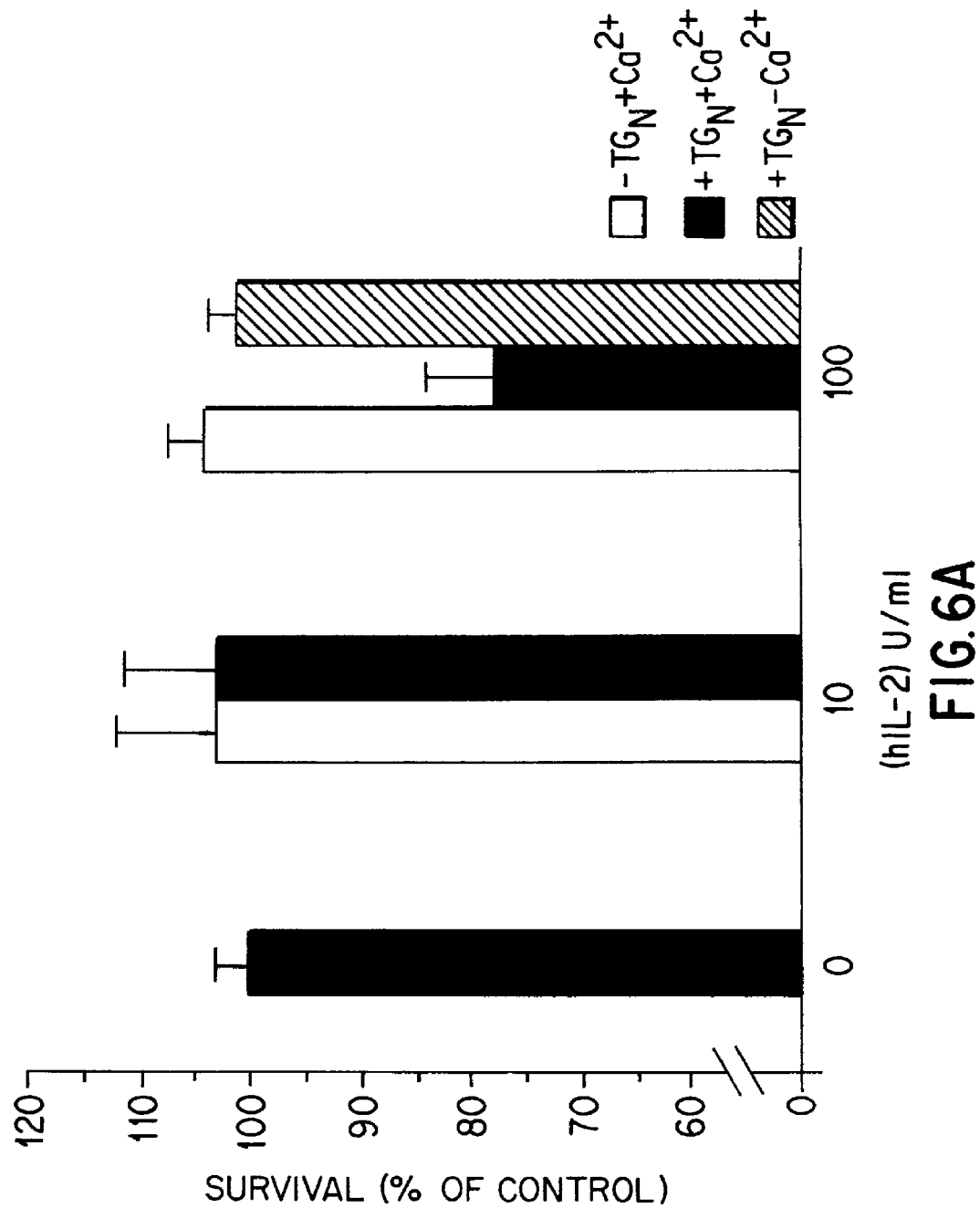

FIG. 9(A)

Reaction A

1. LEFT PRIMER

Sequence: 5' -CTCGAGAAGCTT ACAGTAACCTCAACTCCTGC-3'
Length: 32    Bp-pos:24    5' extension: CTCGAGAAGCTT

2. RIGHT PRIMER

Sequence: 5' -CTCGAGCTCGAG AGTTAGTGTTGAGATGATGC-3'
Length: 32    Bp-pos:506    5' extension: CTCGAGCTCGAG Reaction B

1. LEFT PRIMER

Sequence: 5' -CTCGAGCTCGAG ATGTACAGGATGCAACTCCT-3'
Length: 32    Bp-pos:48    5' extension: CTCGAGCTCGAG

2. RIGHT PRIMER

Sequence: 5' -CTCGAGCTGCAG AATAGAAGGCCTGATATGTT-3'
Length: 32    Bp-pos:551    5' extension: CTCGAGCTGCAG

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 1 :

```
Lys  Lys  Val  Lys  Tyr  Gly  Gln  Cys  Trp  Val  Phe  Ala  Gly  Val
1                 5                          10
```

( 2 ) INFORMATION FOR SEQ ID NO:2:

( i ) SEQUENCE CHARACTERISTICS:
        ( A ) LENGTH: 10 amino acids
        ( B ) TYPE: amino acid (D) TOPOLOGY: linear (ii) MOLECULE TYPE: peptide (xi) SEQUENCE DESCRIPTION: SEQ ID NO: 2:

```
Asn  Ser  Lys  Leu  Thr  Lys  Lys  Lys  Lys  Lys
1              5                        10
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: synthetic DNA (ix) FEATURE:
        (A) NAME/KEY: Restriction Sites
        (B) LOCATION: 1 to 12
        (D) OTHER INFORMATION: base pair position 24 of human
            lymphocyte- derived IL-2 DNA sequence, Taniguchi et al.,
            Nature 302:305-10 (1983)

(xi) SEQUENCE DESCRIPTION: SEQ ID NO: 3:

```
CTCGAGAAGC  TTACAGTAAC  CTCAACTCCT  GC                            32
```

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: synthetic DNA (ix) FEATURE:
        (A) NAME/KEY: Restriction Sites
        (B) LOCATION: 1 to 12
        (D) OTHER INFORMATION: base pair position 506 of human
            lymphocyte- derived IL-2 DNA sequence, Taniguchi et al.,
            Nature 302:305-10 (1983)

(xi) SEQUENCE DESCRIPTION: SEQ ID NO: 4:

```
CTCGAGCTCG  AGAGTTAGTG  TTGAGATGAT  GC                            32
```

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: synthetic DNA (ix) FEATURE:
        (A) NAME/KEY: Restriction Sites
        (B) LOCATION: 1 to 12
        (D) OTHER INFORMATION: base pair position 48 of human
            lymphocyte- derived IL-2 DNA sequence, Taniguchi et al.,
            Nature 302:305-10 (1983)

(xi) SEQUENCE DESCRIPTION: SEQ ID NO: 5:

```
CTCGAGCTCG  AGATGTACAG  GATGCAACTC  CT                            32
```

(2) INFORMATION FOR SEQ ID NO:6:

(i) SEQUENCE CHARACTERISTICS:
        (A) LENGTH: 32 base pairs (B) TYPE: nucleic acid
(C) STRANDEDNESS: single
(D) TOPOLOGY: linear (i i) MOLECULE TYPE: synthetic DNA (i x) FEATURE:
(A) NAME/KEY: Restriction Sites
(B) LOCATION: 1 to 12
(D) OTHER INFORMATION: base pair position 551 of human lymphocyte- derived IL-2 DNA sequence, Taniguchi et al., Nature 302:305-10 (1983)

(x i) SEQUENCE DESCRIPTION: SEQ ID NO: 6 :

CTCGAGCTGC AGAATAGAAG GCCTGATATG TT  32

NERVE-DERIVED TRANSGLUTAMINASE ENZYME

This is a Divisional of application Ser. No. 08/099,759, filed Jul. 30, 1993, now U.S. Pat. No. 5,514,565, which is a continuation-in-part of U.S. Ser. No. 07/840,783, filed Feb. 24, 1992, now abandoned, which is a continuation-in-part of U.S. Ser. No. 07/573,580, filed Aug. 27, 1990, now abandoned, the entire contents of each of which applications are hereby incorporated entirely by reference.

FIELD OF THE INVENTION

The present invention relates to a new nerve-derived transglutaminase (designated hereinafter $TG_N$) and to mammalian enzymatically-produced dimeric interleukin-2 (IL-2), which is cytotoxic to oligodendrocytes, to their preparation and to their use for inducing and facilitating nerve regeneration in mammals.

BACKGROUND OF THE INVENTION

Adult nerves of the mammalian central nervous system (CNS) show poor regenerative ability after axonal injury. Spontaneous growth of injured axons does occur, but ceases after a few hundred microns without traversing the site of the injury and elongating in the distal stump. The failure to regenerate has been attributed to the inhospitable nature of the nerve's environmental milieu, including the inability of astrocytes (the scar-forming cells) to support growth, the paucity of macrophages and/or their products, and the formation of mature oligodendrocytes which inhibit axonal growth.

We recently showed that in a spontaneously regenerating system, e.g., adult fish optic nerve, both the response to injury and the process of regeneration are associated with the presence of a factor(s), that we designated oligodendrocyte cytotoxic factor (OCF), which is selectively cytotoxic to oligodendrocytes of both fish and rats (Published European Application EP No. 415321; Cohen et al., 1990; Sivron et al., 1991). This fish-derived factor was later identified by us as an IL-2-like molecule, with a molecular weight of 28 kDa as compared to 15 kDa in human immune IL-2 and 14 kDa in fish lymphocyte-derived IL-2 (Published European Application EP No. 501445; Eitan et al., 1992). This difference in molecular weight between OCF and IL-2 raised questions with regard to the origin of the factor, i.e., whether it is locally modified IL-2—derived from resident cells in the nerve or from inflammatory cells—or the product of a gene distinct from the gene encoding for immune IL-2 but sharing high homology with it.

It has now been found according to the present invention that an enzyme, identified as a member of the transglutamznase family and found at elevated levels after optic nerve injury in the fish but not in mammal., plays a role in modifying IL-2, possibly by cross-linkage of two molecules, in such a way as to produce the high molecular weight IL-2-like substance observed in the injured fish optic nerve. This new nerve-derived transglutaminase, herein designated $TG_N$, causes dimerization of IL-2, thereby rendering it cytotoxic to oligodendrocytes.

SUMMARY OF THE INVENTION

The present invention relates to enzymatically-producible dimeric IL-2 exhibiting oligodendrocyte cytotoxic activity. The invention further provides means and a method for enzymatically producing directly from mammalian IL-2 a dimeric IL-2 having oligodendrocyte cytotoxic activity.

Since the oligodendrocyte cytotoxic factor and the IL-2-like substance were detected earlier in media conditioned by the injured fish optic nerve, but not in media conditioned by the intact fish optic nerve (EP 415321 and EP 501445), the machinery for local processing of IL-2 and its modification to the dimeric form having oligodendrocyte cytotoxic activity was sought for in the injured fish optic nerve.

It was found according to the present invention that an enzyme of the transglutaminase family is obtainable from injured fish optic nerve. This nerve-derived transglutaminase ($TG_N$) converts mammalian IL-2 to dimeric IL-2 having oligodendrocyte cytotoxic activity.

The invention thus further relates to the enzyme $TG_N$, which is water-soluble, has a molecular weight of about 55 kDa as analyzed by sodium dodecyl sulfate-polyacrylamide gel electrophoresis (SDS-PAGE) and silver staining, and is detected at elevated levels in the injured fish optic nerve, as compared with intact fish optic nerve. $TG_N$ may be purified by affinity chromatography of conditioned medium of injured fish optic nerve with antibodies raised against a peptide corresponding to a well-conserved active site epitope of tranaglutaminasse.

The invention further provides a process for the enzymatic production of mammalian, including human, dimeric IL-2 having oligodendrocyte cytotoxic activity which comprises incubation of mammalian, including human, IL-2, with the enzyme $TG_N$ of the invention.

The monomeric IL-2 used according to the present invention as substrate of $TG_N$ includes native and recombinant IL-2 of any species, preferably mammalian IL-2, most preferably human IL-2, and may be produced by any convenient technique, such as by the process of Robb et al., 1983. It is preferably obtained by recombinant DNA technologies, for example as described by Taniguchi et al., 1983, or Devos, R., 1983. Recombinant murine and human IL-2 are preferably used according to the invention.

As mentioned before, the oligodendrocyte cytotoxic factor originating from the fish optic nerve, originally disclosed in EP No. 415321, was later purified from the conditioned medium of regenerating fish optic nerve (herein regenerating fish conditioned medium) and shown to be an IL2-like molecule (EP No. 501445), as confirmed by the following: (i) antibodies against IL-2 neutralized the oligodendrocyte cytotoxic activity of the regenerating fish conditioned medium; (ii) Western blot analysis revealed the presence of an IL-2 immunoreactive band of 28 kDa in the regenerating fish conditioned medium; (iii) the factor was purified by affinity chromatography from the regenerating fish conditioned medium using anti-IL-2 antibodies; and (iv) recombinant mouse IL-2 had a selective cytotoxic effect in vitro on oligodendrocytes but not on astrocytes. The oligodendrocyte cytotoxic factor might correspond to the dimeric IL-2 of the present invention.

The enzymatically-producible dimeric mammalian IL-2 of the present invention has the following characteristics:

(i) it is water-soluble;
(ii) it is a covalent dimer of IL-2;
(iii) it is selectively toxic to the oligodendrocyte lineage, but not to other cells, such as type-1 astrocytes and fibroblast cells;
(iv) its cytotoxic activity to oligodendrocytes is neutralized by antibodies directed against IL-2;
(V) it is obtainable from mammalian IL-2 by incubation with a nerve-derived transglutaminase; and
(vi) it has a molecular weight of about twice the molecular weight of the substrate mammalian IL-2 as determined by Western blot analysis.

In a preferred embodiment, the enzymatically-produced mammalian dimeric IL-2 according to the invention is human dimeric Il-2 having a molecular weight of about 30 kDa.

The nerve-derived transglutaminase $TG_N$ of the present invention has the following characteristics:

(i) it is water-soluble;

(ii) it is obtainable from regenerating fish optic nerve;

(iii) it converts immune IL-2 to dimeric IL-2 having oligodendrocyte cytotoxic activity;

(iv) it has a molecular weight of about 55 kDa as determined by SDS-PAGE and silver staining;

(V) it is detected at elevated levels in injured fish optic nerve as compared with intact fish optic nerve;

(vi) it incorporates putrescine to a carrier protein in the assay characteristic of the transglutaminase family;

(vii) it is optimally active in the incorporation of putrescine at pH 9 and at 56° C.;

(viii) its $K_m$ in the incorporation of putrescine is $5.5 \times 10^{-7}$ calculated as a function of substrate;

(ix) it is a $Ca^{2+}$-dependent enzyme as regards the IL-2 dimerization process; and (x) it shows an immunoreactive band in Western blot analysis with antibodies raised against peptides corresponding to two sites of transglutaminases, said peptides being selected from a 14-mer corresponding to the active site of transglutaminases, of the sequence:

Lys-Lys-Val-Lys-Tyr-Gly-Gln-Cys-Trp-Val-Phe-Ala-Gly-Val and a 10-mer of the sequence:

Asn-Ser-Lys-Leu-Thr-Lys-Lys-Lys-Lys-Lys.

Both the enzymatically-produced dimeric IL-2 and the nerve-derived transglutaminase $TG_N$ according to the invention, each of them alone or in combination, are for use in pharmaceutical compositions for inducing and facilitating regeneration of injured nerves of the central nervous system (CNS) in mammals, including humans. The preparation of such compositions is described in EP No. 415321 and EP No. 501445. The compositions comprising the dimeric IL-2 or the enzyme $TG_N$ or both enable injured nerves to be treated in vivo by selective elimination of oligodendrocytes, normally an obstacle to regeneration in mammalian CNS, thereby facilitating the growth of axons in their own environment.

BRIEF DESCRIPTION OF THE DRAWINGS

FIG. 6A–D show that IL-2 activity shifts toward cytotoxicity against oligodendrocytes following dimerization mediated by $TG_N$. Enriched oligodendrocyte cultures were treated with various preparations containing either $TG_N$ alone, hIL-2 preincubated with $TG_N$, or hIL-2 alone. Cytotoxic activity (in terms of the number of surviving cells) was assessed by the calorimetric MTT[3-(4,5-dimethylthiazol-2-yl)-2,5-diphenyltetrazolium bromide] assay. Panel A shows the quantitative analysis (absorbance at 540 nm against absorbance at 630 nm) of various cultures treated with 10 or 100 U/ml of hIL-2 in the presence or absence of $TG_N$, after MTT staining. Panel B : micrograph of cultures treated with hI-2 only (100 U/ml); Panel C : micrograph of cultures treated with $TG_N$ only; Panel D : micrograph of cultures treated with a mixture of hIL-2 (100 U/ml) and $TG_N$ (containing the enzymatically-produced dimeric hIL-2).

FIG. 9A–9B depict design and construction of human IL-2 cDNA products by PCR. FIG. 9A depicts the two sets of primers, including the added restriction sites (dashed boxes), used to construct the human IL-2 cDNA products (Bp-pos refers to the position of the primer on the human lymphocyte-derived IL-2 cDNA sequence). FIG. 9B depicts the two PCRs employed to produce copies of the two different monomeric IL-2 cDNAs used to construct the linear dimeric IL-2.

FIG. 11A shows two dilutions (1:3, lanes 1, 3, 5, and 1:9, lanes 2, 4, 6) of medium collected from infected Vero cells (lanes 1, 3). Infected Vero cell extracts (lanes 2,4) and medium and cell extracts obtained from cells infected by the defective virus only (lanes 5 and 6, respectively) were electrophoresed on sodium dodecyl sulfate-polyacrylamide gel electrophoresis (SDS/PAGE). Arrows point to the IL-2 immunoreactive bands in each slot. FIG. 11B indicates the commercial monomeric IL-2 (lane 2) and the dimeric IL-2 (lane 1), synthesized by the nerve-derived transglutaminase and used as size controls. Molecular markers were electrophoresed on the same gels and their positions are indicated.

FIG. 12 shows that linear dimeric IL-2 is not cytotoxic to oligodendrocytes. Cytotoxic activity against oligodendrocytes, assessed by the calorimetric MTT assay, was examined by application of aliquots from the samples described in FIG. 11, at different dilutions (left panel). The results were compared to parallel experiments (right panel) in which oligodendrocytes were treated either with soluble substances derived from regenerating optic nerves (CM) in which the cytotoxic IL-2-like factor was identified with enzymatically-synthesized human dimeric IL-2. Both of these treatments caused a significant reduction (by ANOVA: dimeric IL-2, F=7.833; CM, F=104.976; P=0.02 and P=0.0001, respectively, according to Fisher comparison) in the number of mature oligodendrocytes. The experiment, which was repeated three times, was performed in triplicate. Results are presented as means±SD of the untreated culture values, representing 100% survival.

FIG. 13 shows that linear dimeric IL-2 causes proliferation of CTLL-2 cells. Biological activity on CTLL-2 cells, assayed by thymidine incorporation, was examined by application of aliquots from the samples described in FIG. 11 (left panel). The results were compared with those of a parallel experiment (right panel) in which CTLL-2 cells were treated with commercial monomeric human IL-2 as a control. The experiment was performed in triplicate. Results are presented in cpm.

DESCRIPTION OF THE PREFERRED EMBODIMENTS

In accordance with the present invention, a nerve-derived enzyme of 55-kDa, identified as a member of the transglutaminase family, was found in elevated levels in regenerating fish optic nerves and to be involved in dimerization of IL-2. Dimerization might play an important role after axonal injury as a mechanism for changing the activity of factors so as to satisfy the injury-induced conditions needed for regeneration. For example, postinjury cytotoxicity to oligodendrocytes may be of importance in eliminating mature oligodendrocytes, known to inhibit axonal growth and elongation. Accordingly, injury-induced elevation of an enzyme that can alter IL-2 activity, thereby enhancing its cytotoxicity to oligodendrocytes, might be one of the factors to explain the results observed here.

The transglutaminases, a protein family of wide tissue distribution, are reportedly associated with stabilization of proteins, thereby increasing their resistance to chemical, enzymatic and physical degradation. Enzymes of this family were found in plasma and extracellular fluids, and proteins modified by these enzymes were detected in the fibrin network of blood clots, in cell membranes, in extracellular matrices and in cornified features (Greenberg et al., 1991). The transglutaminase enzyme $TG_N$ of the present invention was found under nerve injury conditions and, for the first time, was purified from the nervous system. Purification was achieved by affinity chromatography with antibodies directed against a well-conserved epitope, i.e., the active site of known transglutaminases from other tissues and species. It thus seems that the fish nerve-derived transglutaminase also possesses this conserved sequence, or at least a closely homologous sequence, thus explaining its activity on human-derived proteins, i.e., hIL-2. Variations in sequence beyond the active site cannot be excluded at this stage, and might be unique to the nervous system, but transglutaminases of other origins and species may be active as well and are also encompassed by the invention.

Up to now, the most effective approach used to circumvent the oligodendrocyte inhibitory effect has involved the use of antibodies specific to the inhibitors (Schnell and Schwab, 1990). The availability of $TG_N$ opens the way to the preparation of a factor cytotoxic to oligodendrocytes of all species, by incubation of recombinant IL-2 of any species with the enzyme $TG_N$.

It is possible that mammals are deficient not in IL-2 itself, but in the enzyme needed for its posttranslational modification. The enzymatically-produced dimeric IL-2, corresponding to the oligodendrocyte cytotoxic factor, seems to be the reactive form needed in order to eliminate oligodendrocytee from a mature nerve after injury, thereby making the nerve more conducive to axonal growth.

Thus, according to the invention, evidence is provided for a mechanism in which an active factor (IL-2) is converted into a form (enzymatically-produced IL-2 dimer) having a different type of activity. In order to check whether the structure of the dimerized protein plays a role in its conversion into an active factor, or whether any configuration of the dimer (linear, for example) would do, we constructed a defective viral vector of herpes simplex virus (HSVl) that expresses high levels of linear dimerized IL-2 protein. In contrast to the enzymatically-synthesized dimeric IL-2, in which the monomeric protein is converted into a dimeric form by posttranslational modification, the linear dimeric IL-2 protein thus constructed was designed at the transcriptional level and was thus a product of translation. Using this approach, we were able to obtain high levels of a linear dimeric IL-2 protein that was released into the medium following its synthesis, even though the defective virus itself remains in the cells and continues to express the inserted protein.

The linear IL-2 dimer has a different structure from that of the IL-2 dimer produced enzymatically and was then used to show that the cytotoxic property of the protein is a function of its structural conformation. The linear dimeric IL-2 produced by genetic engineering technique retained the biological activity of monomeric IL-2, but failed to exhibit the oligodendrocyte cytotoxic activity exerted by IL-2 dimerized enzymatically, indicating that the conversion of IL-2 into a dimeric form exhibiting a specific type of activity is structurally dependent.

In addition, $TG_N$ itself can cause regenerative growth within the nerve's own environment in transected nerves of mamalian CNS leading to functional recovery. Although the example given here is of a transglutaminase derived from fish optic nerve, it is intended that all transglutaminases, particularly nerve-derived transglutaminames are encompassed by the invention.

The invention will now be illustrated by the following non-limiting examples.

EXAMPLES

Example 1
Conditioned medium of injured fish optic nerve can modify IL-2 with respect to its molecular weight.

Since oligodendrocyte cytotoxic factor is present in media conditioned by injured fish optic nerve, and oligodendrocyte cytotoxic factor was found to be an IL-2-like molecule of molecular weight of about 28 Kd, whose cytotoxic activity is neutralized by anti-IL-2 antibodies, it was then examined whether the fish injured nerve carries a substance, probably an enzyme, that can modify mammalian IL-2 of low molecular weight to a high molecular weight form of IL-2. Media conditioned by regenerating fish optic nerves were examined for the presence of a mechanism for the posttranslational modification of exogenously added IL-2. Accordingly, human recombinant IL-2 (hIL-2) was incubated with the conditioned media (CM) in the presence of 5 mM $Ca^{2+}$ or in its absence, and the resulting products were subjected to Western blot analysis with the aid of antibodies directed against IL-2.

For this purpose, CM of regenerating fish optic nerves was prepared as previously described by Eitan et al., 1992. Briefly, carp were anesthetized with 0.05% 3-aminobenzoic acid ethyl ester (Sigma) and the right optic nerves were crushed with forceps (for 30 sec), excised 6–7 days later and incubated in serum-free medium (1.5 hours at 25° C., 4 nerve segments in 300 µl medium). The resulting media (CM) were collected and their protein content determined by the Bradford method.

Aliquots of 6 µg CM were incubated overnight with hIL-2, while being gently shaken with 5 mM $CaCl_2$. The mixture was subjected to SDS-PAGE (12% acrylamide). The gel was blotted onto nitrocellulose for 2 hours at 200 mA, and the nitrocellulose incubated overnight at 4° C. with phosphate-buffered saline (PBS) containing 5% (wt/vol) milk, and then washed in PBS. The blot was incubated with IL-2 antibodies for 2 hours at 37° C., then washed three times for 5 min in PBS containing 0.05% Tween-20, and finally with horseradish peroxidase (HRP)-conjugated goat anti-rabbit IgG for 2 hours at room temperature. Visualization of the immunoreactive bands was accomplished by ECL (Amersham).

Figure 1:
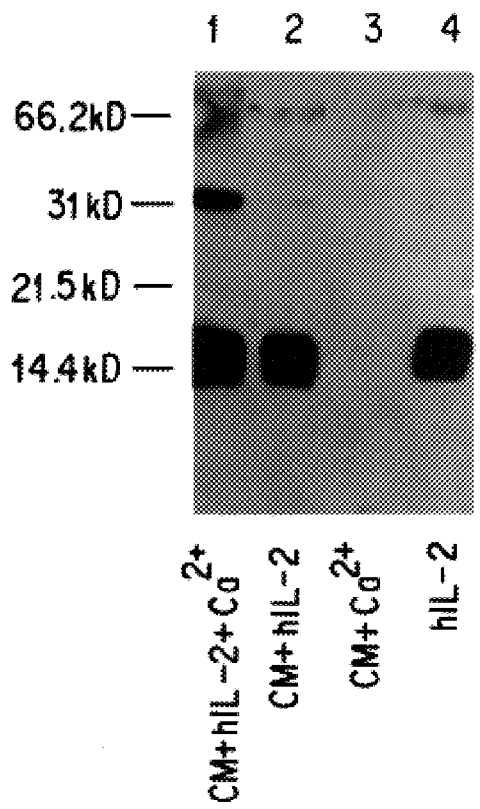
FIG. 1 shows the ability of conditioned medium (CM) of regenerating fish optic nerves to dimerize human IL-2 (hIL-2). Aliquots of CM were incubated overnight with hIL-2, and the mixture was subjected to SDS-PAGE (12% acrylamide), followed by Western blot using IL-2 antibodies. Visualization of the immunoreactive bands was accomplished by ECL (Amersham). Lanes: 1, CM incubated with hIL-2 in the presence of $Ca^{2+}$; 2, CM incubated with hIL-2 in the absence of $Ca^{2+}$; 3, CM only in the presence of $Ca^{2+}$; 4, hIL-2 only. Molecular weight markers were electrophoresed on the same gel and their positions are indicated.

The results are shown in FIG. 1, wherein : Lane 1, CM incubated with hIL-2 in the presence of $Ca^{2+}$; Lane 2, CM incubated with hIL-2 in the absence of $Ca^{2+}$; Lane 3, CM only in the presence of $Ca^{2+}$; Lane 4, hIL-2 only in the absence of $Ca^{2+}$. Molecular weight markers were electrophoresed on the same gel and their positions are indicated. In the slot containing only hIL-2, one immunoreactive band of 15 kDa was found. Following incubation with CM, an additional IL-2 immunoreactive band having a molecular weight twice as high as that of the original IL-2 compound could be detected. These results raised the possibility that the regenerating nerve possesses the machinery to dimerize IL-2. The high molecular weight IL-2 immunoreactive band was not observed when $Ca^{2+}$ was omitted from the incubation mixture (FIG. 1, lane 2), suggesting that the dimerization process is mediated by a $Ca^{2+}$-dependent enzyme.

Example 2
Transglutaminase immunoreactivity in fish optic nerves is elevated after injury In view of these findings, we considered the possibility that the agent responsible for modifying the IL-2 is an enzyme that is selectively elevated after injury, and that the effect of the enzyme is to achieve dimerization of the IL-2 molecule. The enzyme transglutaminase was considered as a potential candidate, as it is known to be involved in cross-linking of proteins (Greenberg et al., 1991); moreover, in the regenerating fish optic nerve it was proposed that an activity reminiscent of transglutaminase is elevated (Chakrabarty et al., 1987).

Antitransglutaminase antibodies were elicited in rabbits against each of a synthetic peptide of 10 and 14 amino acids bound to bovine serum albumin. The peptides, of the sequence Asn-Ser-Lys-Leu-Thr-Lys-Lys-Lys-Lys-Lys, or Lys-Lys-Val-Lys-Tyr-Gly-Gln-Cys-Trp-Val-Phe-Ala-Gly-Val, correspond to known sequences of transglutaminases of other species and tissues. The 14-mer peptide represents the active site of transglutaminases.

Western blot analysis confirmed the presence of a 55-kDa transglutaminase-immunoreactive band in the regenerating fish optic nerve. The gel was blotted as described in Example 1. CM (20 µg) and high speed supernatant of regenerating optic nerves (HSS-C; 16 µg) and high speed supernatant of normal non-injured nerves (HSS-N; 20 µg) were electrophoresed on SDS-PAGE (10% acrylamide). The blot was incubated with antibodies prepared against the above-mentioned conserved 14-mer peptide for 2 hours at room temperature, and then washed three times for 5 min in PBS containing 0.05% Tween-20. Finally, the blot was incubated for 2 hours at 37° C. with HRP-conjugated goat anti-rabbit antibodies. Visualization was accomplished by ECL (Amersham).

Figure 2:
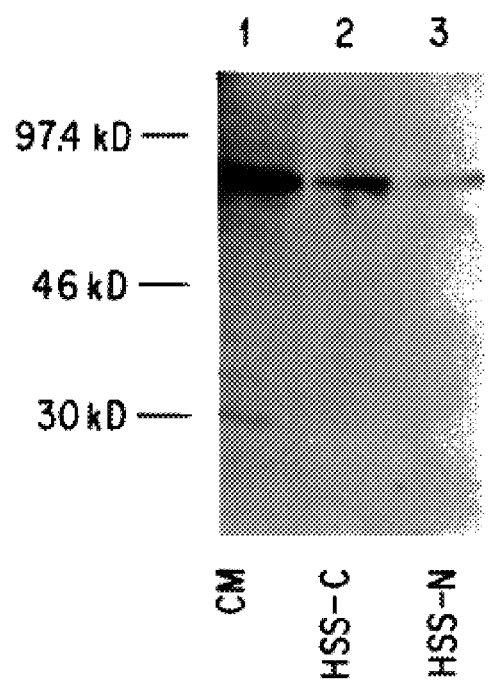
FIG. 2 shows Western blot analysis revealing the presence of a transglutaminase immunoreactive protein of 55 kDa in regenerating fish optic nerves. CM, high speed supernatant of regenerating optic nerves (HSS-C) and high speed supernatant of normal non-injured nerves (HSS-N) were electrophoresed on SDS-PAGE (10% acrylamide). The blot was incubated with antibodies prepared against the conserved 14-amino acid sequence of the transglutaminase enzyme family. Visualization was accomplished by ECL (Amersham). Lanes: 1, CM; 2, HSS-C; 3, HSS-N.

The results are shown in FIG. 2, wherein : Lanes: 1, CM; 2, HSS-C; 3, HSS-N. The 55-kDa immunoreactive band was observed in CM and in HSS. Densitometric analysis revealed that the intensity of the 55-kDa immunoreactive band is 3-fold higher in HSS-C than in HSS-N.

Example 3
Purification of fish optic nerve transglutaminase

In order to verify that this transglutaminase-immunoreactive protein is responsible for the observed modification of IL-2, it was purified as follows : Carp (Cyprinus carpio) optic nerves (n=60) were excised 6–7 days after crush injury and homogenized in a buffer of 10 mM Tris-HCl, pH 7.4, containing 1.5 mM $CaCl_2$, 1 mM spermidine, 25 µg/ml aprotinin, 25 µg/ml leupeptide and 5 µg/ml pepstatin. Sucrose was added to the homogenate to obtain a final concentration of 0.25M. The high speed supernatant (HSS) was collected after centrifugation for 1 h at 4° C. at 150,000 g, and its protein content was determined by the Bradford method. The HSS was then eluted through an affinity column of poly-L-lysine (PLL) coupled to agarose, and the resultant eluate (Eluate PLL) was subjected to an additional affinity column of the affinity-purified rabbit antibodies prepared as described above against the conserved 14-mer peptide of transglutaminase. Bound substances were eluted from the column with 0.2M glycine, pH 2.7, neutralized with 1M Tris, pH 8.0, and their protein content determined (Eluate TG Ab). The purification steps are summarized in Table 1.

TABLE 1

Purification of fish optic nerve transglutaminase

| Purification Steps | Yield/mg | Purification degree |
| --- | --- | --- |
| Crude homogenate | 14 | 1 |
| Eluate PLL | 1.8 | 7.8 |
| Eluate TG Ab | 0.004 | 3500 |

Figure 3:
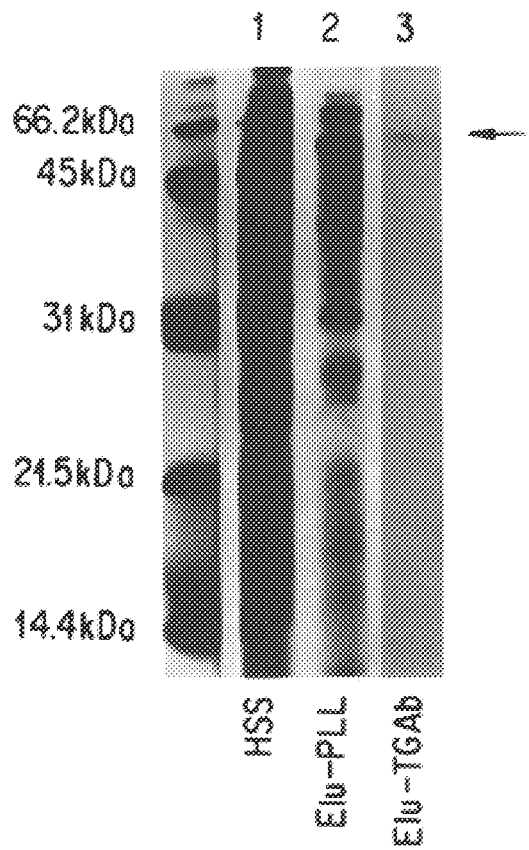
FIG. 3 depicts SDS-PAGE showing the stepwise purification of fish optic nerve transglutaminase ($TG_N$). Lanes: 1, HSS; 2, Elu-PLL (eluate from PLL-agarose column); 3, Elu - TG Ab (eluate from anti-transglutaminase affinity column).

The proteins eluted from the transglutaminase affinity column were subjected to 10% SDS-PAGE to verify their purity. FIG. 3 is SDS-PAGE showing the stepwise purification of fish optic nerve transglutaminase ($TG_N$). Following each step, the resulting preparation was subjected to SDS-PAGE, and the gel was stained for visualization of the analyzed proteins by silver staining. Lanes: 1, HSS; 2, Elu-PLL; 3, Elu-TG Ab. As shown, a single band of 55 kDa is obtained after the last step of purification.

The enzyme $TG_N$ can be purified also from the conditioned medium of regenerating fish optic nerve by applying it to an affinity column of PLL coupled to agarose, followed by subjecting the eluate to an additional affinity column of the antibodies and elution, as described above for the homogenate.

Example 4
Incorporation of putrescine to casein mediated by $TG_N$

The incorporation of radioactive putrescine to a carrier protein is an assay characteristic of enzymes of the transglutaminase family. Any carrier protein that has lysine residues may be used in the assay, such as casein, bovine serum albumin, etc.

In this example, activity characteristic of the nerve-derived transglutaminase was measured by incorporation of [$^{14}$C] putrescine into N,N-dimethylcasein (Chakrabarty et al., 1987). The purified $TG_N$ enzyme eluted from the TG-Ab affinity column with glycine in Example 3 was dialyzed for 2 hours in the presence of N,N-dimethylcasein (1 mg/ml), before being added to the reaction mixture. The reaction was initiated by addition of crude $TG_N$ (07–10 ng), followed by incubation for 20 min at 37° C. and terminated by the addition of ice-cold trichloroacetic acid (TCA; final concentration, 5%). Specific activity value of $TG_N$ is 502000±115000 ([$^{14}$C] putrescine/µg protein; cpm) (n=3, two purifications, three assays).

Figure 4A:
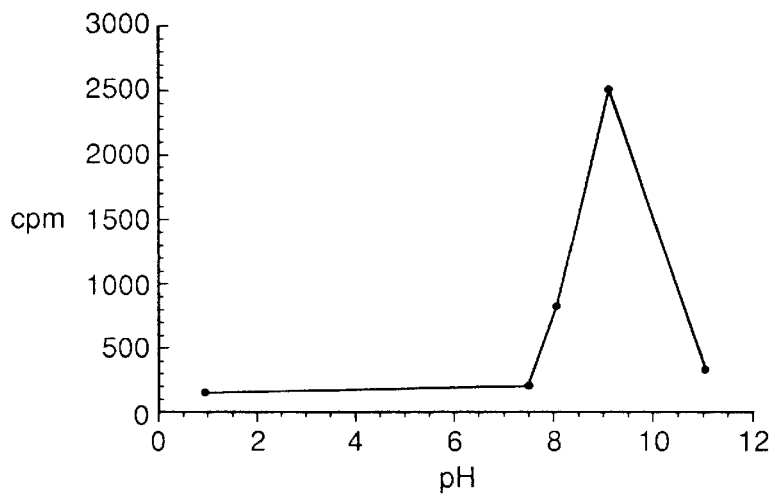
FIG. 4A–C illustrate biochemical characterization of the enzyme $TG_N$. Panel A shows putrescine incorporation to casein mediated by $TG_N$ as a function of pH; Panel B shows putrescine incorporation to casein mediated by $TG_N$ as a function of temperature; and Panel C illustrates determination of $K_m$ of $TG_N$ by Scatchard plot analysis.
Figure 4B:
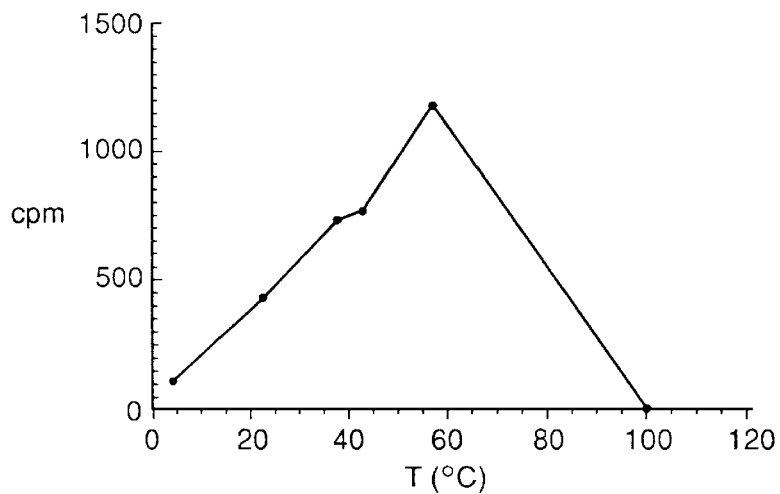
Figure 4C:
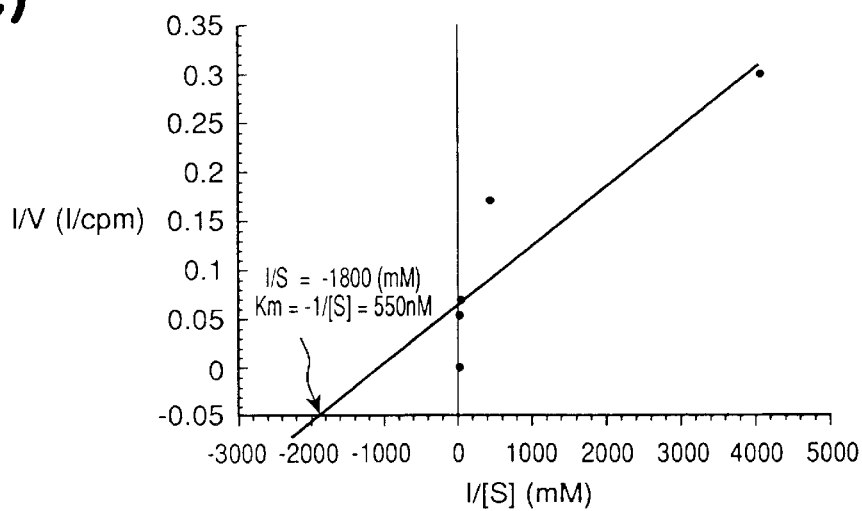
Figure 6B:
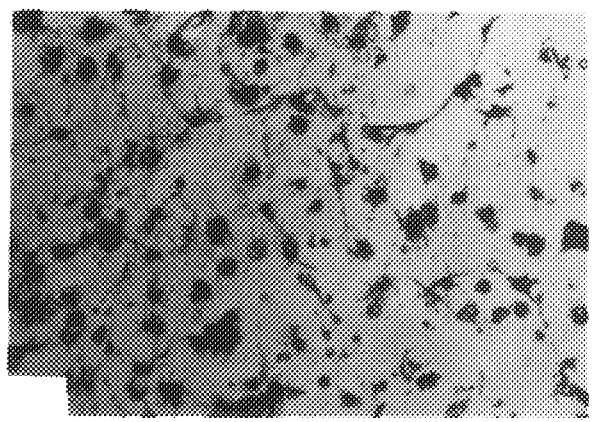
Figure 6C:
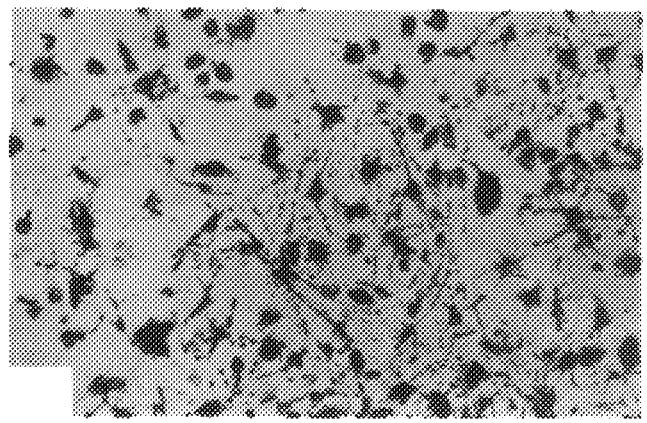
Figure 6D:
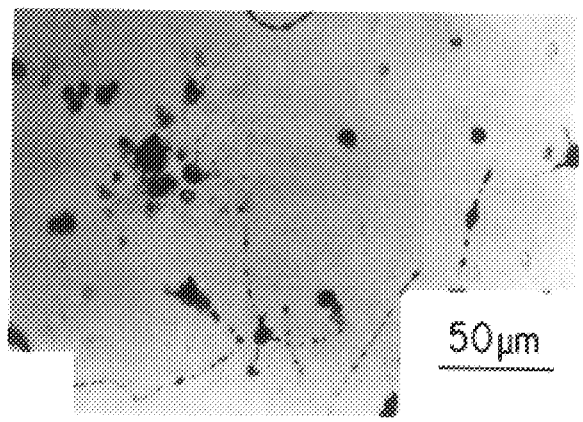

The enzyme activity was titrated with respect to temperature and pH and substrate concentration. As shown in FIG. 4A and 4B, respectively, the optimal activity of $TG_N$ was found at pH around 9 and at 56° C. The $K_m$ was calculated from the titration of activity as a function of substrate concentration and was found to be $5.5 \times 10^{-7}$M. Titration was carried out by measuring incorporation of [$^{14}$C] putrescine to caseine in the presence of $TG_N$.

Example 5
Purified fish optic nerve transglutaminase dimerizes human IL-2

The ability of the purified enzyme of Example 3 to dimerize IL-2 was examined. Human recombinant IL-2 (hIL-2) was incubated as described in Example 1, except that in this experiment purified $TG_N$ was used rather than the crude CM. As controls, hIL-2 or the purified enzyme $TG_N$ were incubated separately in the same buffer. All incubations were carried out in the presence of 5 mM $Ca^{2+}$ and 0.3% heat-inactivated fetal calf serum (FCS).

Figure 5:
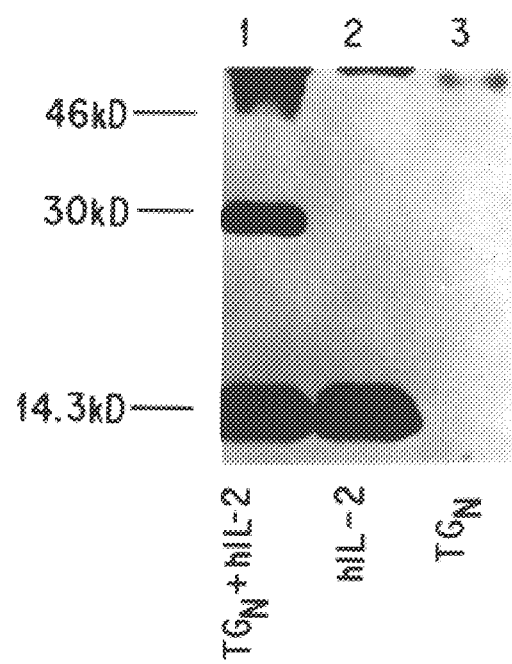
FIG. 5 shows that purified $TG_N$ dimerizes hIL-2. Lanes: 1, purified $TG_N$ incubated with hIL-2; 2, hIL-2 only; 3, $TG_N$ only. The experiment was carried out as described in FIG. 1, except that purified $TG_N$ was substituted for the CM. All incubations were carried out in the presence of 5 mM $Ca^{2+}$.

Following the incubation the mixture was applied to analysis by Western blot. Separation was carried out on SDS-PAGE (12% acrylamide) followed by blotting onto nitrocellulose for 2 h at 200 mA. The nitrocellulose was then washed in PBS, first incubated overnight at 4° C. in PBS containing 5% milk, and then further incubated for 2 h at 37° C. with rabbit antibodies directed against human IL-2, followed by 3 washes in PBS containing 0.05% Tween-20. After the last wash, further incubation for 1½ h was carried out at room temperature with goat anti-rabbit antibodies conjugated to horseradish peroxidase (HRP-GaRb), followed by three washes with PBS containing Tween-20 and incubation for 1 min in the Western blotting detection reagent (ECL, Amersham), air drying and exposure to film. The results are shown in FIG. 5, wherein: Lanes: 1, purified $TG_N$ plus hIL-2; 2, hIL-2 only; 3, $TG_N$ only.

As shown in FIG. 5, in addition to the original IL-2, a high molecular weight IL-2 immunoreactive band of 30 kD was obtained. Densitometric analysis revealed that about 25% of the IL-2 was dimerized under these conditions.

Example 6
Enzymatically-produced dimeric IL-2 is cytotoxic to oligodendrocytes To ascertain the biological significance of the dimerization, we examined whether the resulting dimeric IL-2 possessed cytotoxic activity against oligodendrocytes. hIL-2 (at 100 U/ml or 10 U/ml) was incubated with the purified $TG_N$ enzyme and the reaction mixture was then applied to enriched cultures of rat brain oligodendrocytes. Control cultures consisted of untreated oligodendrocytes as well as oligodendrocytes exposed separately to hIL-2 at 100 U/ml of 10 U/ml and to the purified enzyme.

Enriched oligodendrocyte cultures derived from neonatal rat brains were prepared as described by Bottenstein and Sato, 1979, and seeded in wells coated with PLL (20 µg/pl) (Sigma). After 72 hours, the seeded cells were treated with various preparations containing either $TG_N$ alone, hIL-2 preincubated with $TG_N$, or hIL-2 alone. hIL-2 at two different concentrations, 10 U/ml and 100 U/ml, were incubated with a constant amount of $TG_N$. Cytotoxic activity (in terms of the number of surviving cells) was assessed by the colorimetric MTT assay (Sigma) (T. Mosmann, 1983, J. Immunol. Meth. 65:55–63). After incubation for 48 hours with the various preparations, MTT (10 µl, 5 mg/ml) was added for 3 hours; the medium was then removed, and 100 µl of 0.04M HCl in isopropanol was added. The cells were gently shaken until all crystals had dissolved. Their absorbance was recorded at 540 nm against absorbance at 630 nm as reference.

The results are shown in FIG. 6A–D. The micrographs show the various treated cultures after MTT staining. B, Cultures treated with hIL-2 only (100 U/ml); C, cultures treated with $TG_N$ only; D, cultures treated with the mixture of hIL-2 (100 U/ml) and $TG_N$ containing the enzymatically-produced dimeric hIL-2. As can be seen in FIG. 6, only those oligodendrocyte cultures that were treated with the reaction mixture containing the enzymatically-produced dimeric IL-2 exhibited cytotoxicity. From the results shown in FIG. 5 it appears that in the reaction mixture containing dimeric IL-2, 25% of the IL-2 is dimeric and the rest is in a monomeric form. It thus seems that 25 U/ml of IL-2 in the dimeric form is sufficient to exert cytotoxicity under conditions where 100 U/ml of monomeric IL-2 are not cytotoxic.

For the preparation of enriched oligodendrocyte cultures, neonatal rat brains (2 days old) were excised [2 brains in 2 ml of Leibowitz medium (L-15); Gibco] and chemically dissociated by $3 \times 10^4$ U/ml trypsin (Sigma) in DMEM ($Ca^{2+}$ and $Mg^{2+}$ free), containing 1 mM ethylenediaminetetraacetic acid (EDTA). Mechanical dissociation was carried out prior to 10 min incubation at 37° C. with the trypsin solution. The cells were then transferred into 15 ml conical tubes containing 1 ml of solution of 74 U/ml DNase (Sigma), 5200 U/ml soybean trypsin (Sigma) and 3 mg BSA, incubated for 1 min at room temperature, added to 10 ml of medium, and subsequently washed 3 times in DMEM. After the last wash, the cells were suspended in 10 ml DMEM containing 5–10% fetal bovine serum (FBS; Sigma-heat inactivated at 56° C. for 30 min), passed through mesh and seeded in 85 mm² flasks (Nunc), previously coated overnight at 37° C. with 20 μg/ml poly-L-lysine (PLL, MW 100000; Sigma). The medium was changed first twenty-four hours after cell seeding and then once every 2–3 days thereafter. On the 8th day after seeding, the cells were incubated with shaking for 4–6 h, the supernatant was removed and the remaining cells further incubated in 10 ml medium (DMEM plus 5–10% FBS) for several hours followed by an overnight shaking. The cells that were removed by the shaking were collected and centrifuged, and the pelleted cells were then resuspended in 1–2 ml of serum-free medium. The thus obtained enriched oligodendrocyte cultures recovered cells were seeded on 96-well plates previously coated with PLL (20 μg/ml). Cells were seeded with 100 μl of defined medium (Raff's modification to Bottenstein's and Sato's defined medium). After 48–72 h, the seeded cells were treated as described above.

Example 7

$TG_N$ treatment can cause functional recovery of transected adult rat optic nerves Electrodes were implanted in the visual cortex of 30 adult (12–14 week old) Sprague-Dawley (SPD) rats for on-line monitoring of changes in the visual pathway, before and after injury. Anesthetized rats (Rumpon, Vetalar) were placed in a small animal stereotaxic instrument, and two holes were drilled in the exposed skull, with the dura kept intact to minimize cortical damage. One hole, drilled above the nasal bone, was used as reference point. The second hole was in area OC1, with coordinates Bregma –8 mm and lateral 3 mm. The electrodes were gold contact pins (Wire-Pro, Inc.) connected to screws, which were screwed into the holes and cemented to the skull with acrylic cement. The field potential, recorded first in intact nerves and then after injury was evoked by stroboscopic stimulation (Xenon flash tube 4W/sec, 1–2 msec duration, 0.3 Hz), amplified 1000 times (AM Systems, Microelectrode AC amplifier, Model 1800) and digitized (12 bits, 500 samples/sec) (National Instruments, Board MI016-9 and LabView 2.2.1 Data Acquisition and Management System). During recording of the visual evoked potential (VEP) response, the contralateral eye was always covered. One week after the electrodes were implanted, the left optic nerve was exposed by opening of the perineural sheath. The nerve fibers were dissected 2 mm from the globe, without damaging the nerve vascularization, with the aid of a specially designed glass probe with a 200-μm tip and a smooth blunt edge. The nerve was completely transected, and 2 μl of a buffer solution without or with $TG_N$. (designated control and $TG_N$-treated, respectively) was injected into the injury site via a glass pipet. For surgery, treatment and recording, a double-blind protocol was followed. The $TG_N$ employed was purified $TG_{N'}$ prepared from CM according to Example 3.

One week after injury eight out of the 30 animals exhibiting residual VEP activity, probably reflecting incomplete transection, were withdrawn from the experiment and 10 $TG_N$-treated and 12 control animals were left for the rest of the experiment. Six weeks after injury, the VEP response was again recorded from the remaining 22 animals. The VEP response is characterized by two parameters: latency and amplitude of the first negative peak response. In this on-line experiment seven of the 10 $TG_N$-treated injured nerves, which remained for the follow-up as they had no response at 1 week, showed functional recovery (Table 2). In the 12 control animals which were left after 1 week, no recovery was detected 5 weeks later (Table 2).

Peaks of activity in most cases in $TG_N$-treated injured nerves seemed to be shifted, relative to those of uninjured nerves with significant difference between them in terms of both amplitude and latency (Table 3). The amplitude in $TG_N$-treated injured nerves, while always smaller than in intact nerves, was higher than expected, possibly because of arborization to vacant sites in the primary target (the lateral geniculate nucleus) or changes in the nature and amount of neurotransmitters involved in the evoked response.

Figure 7A:
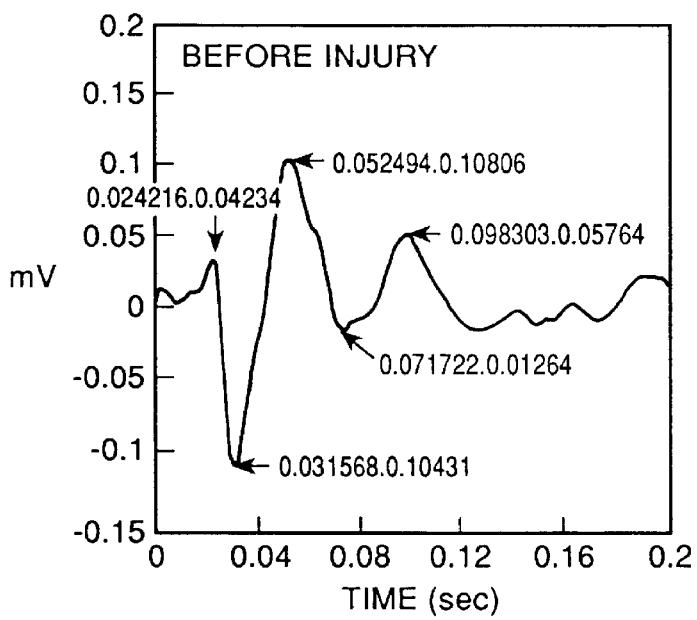
FIG. 7A–C depict on-line recording of functional activity in a $TG_N$-treated injured nerve. The figure presents the results obtained from one representative animal (rat) treated with $TG_N$. Visual evoked potential (VEP) responses were recorded before the injury and 1 and 6 weeks after injury, as described in the specification (Panels A, B and C, respectively). Note that 6 weeks after injury (panel C) the recovery is manifested by small peaks, all shifted relative to those in the uninjured nerve. Values are means obtained from four recordings at each time point (solid line) ±SE (grey line).
Figure 7B:
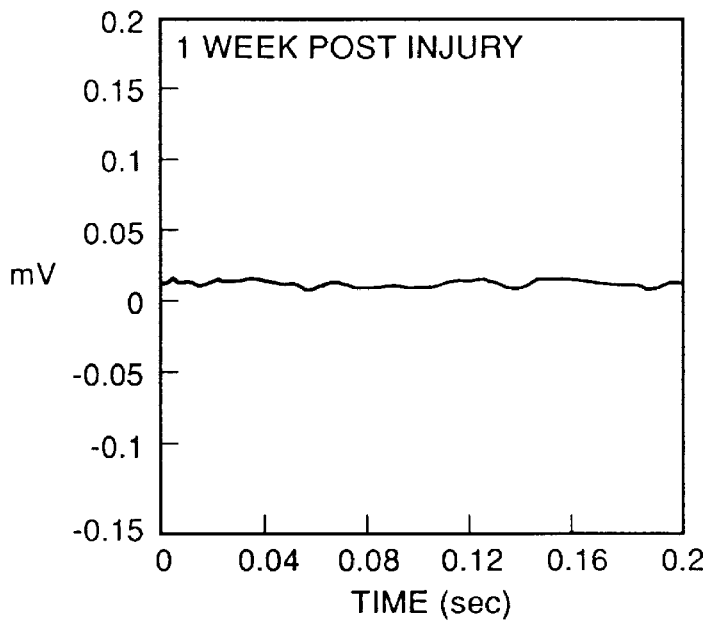
Figure 7C:
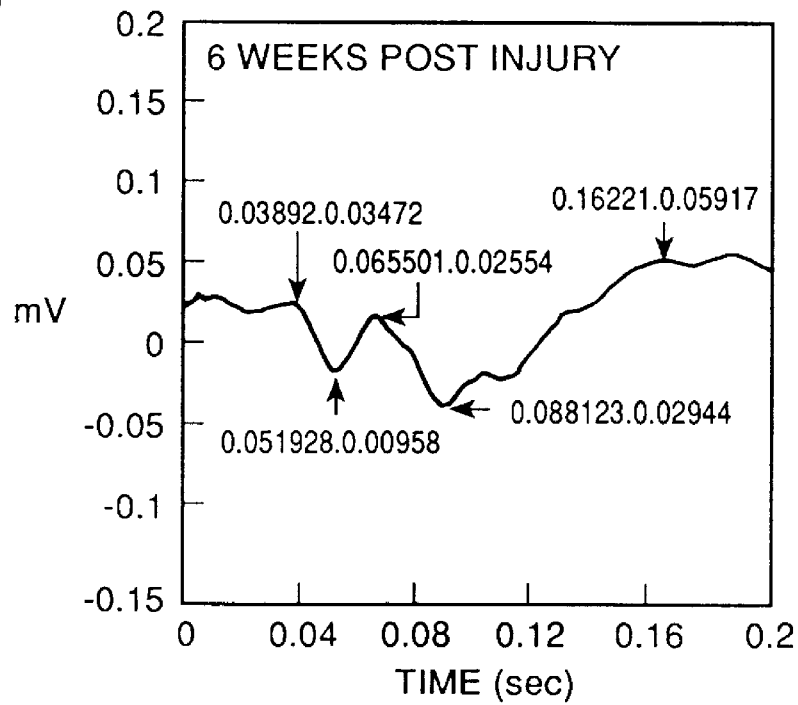

FIG. 7A–C show typical results of on-line recording of functional activity in a $TG_N$-treated injured nerve of a SPD rat. VEP responses were recorded before the injury (panel A) and 1 and 6 weeks after injury (panels B and C, respectively). One week after injury, no VEP response was detectable. Six weeks later, however, positive VEP activity was recorded. The peaks are shifted relative to the preinjured state, thus having longer latencies and smaller amplitudes.

Figure 8A:
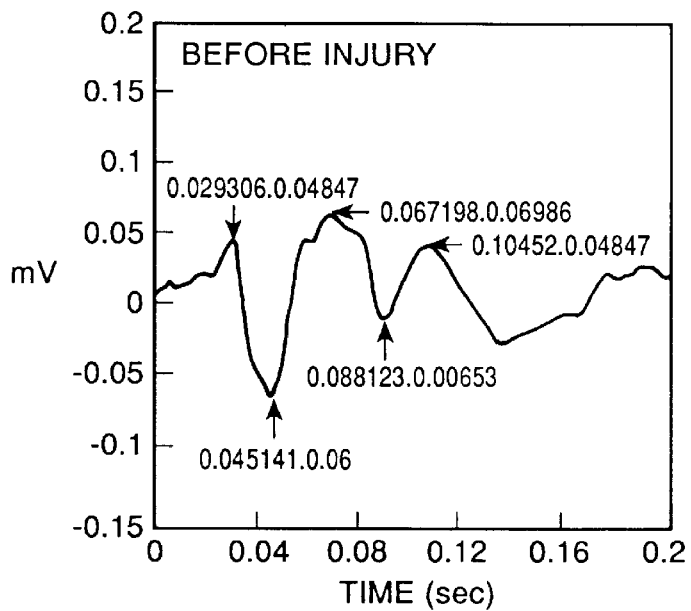
FIG. 8A–C depict on-line VEP response in control (buffer-treated) injured nerves. A representative animal (rat) was treated with buffer and VEP responses were recorded before the injury and 1 and 6 weeks after injury, as described in the specification (Panels A, B and C, respectively). Values are means (solid line) ±SE (grey line).
Figure 8B:
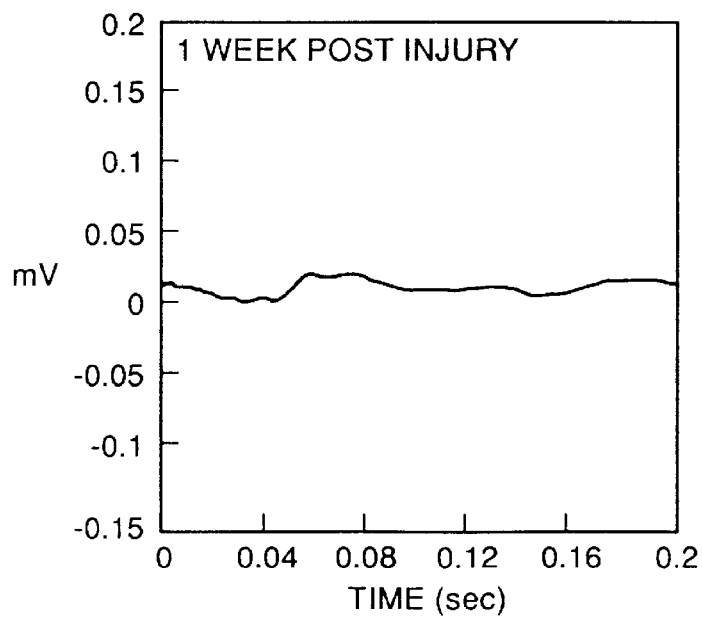
Figure 8C:
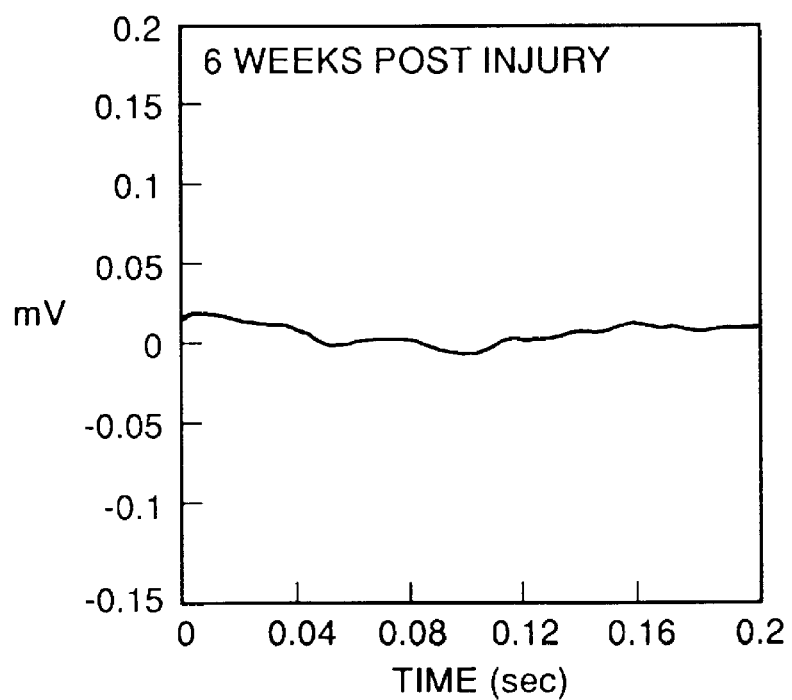

FIG. 8A–C present a typical recording from a control (buffer-treated) animal. The figure shows VEP response acivities in a representative animal recorded before the injury (panel A) and 1 and 6 weeks after injury (panels B and C, respectively). No VEP response could be detected 6 weeks after injury.

TABLE 2

VEP response of individual $TG_N$-treated injured and control animals. The VEP response of each animal was recorded 6 weeks after injury. The latency and amplitude of the first negative peak response are presented. All of these animals showed a complete absence of VEP activity 1 week after injury.

| Treatment | Latency (msec) | Amplitude (μV) |
|---|---|---|
| $TG_N$ | 0 | 0 |
| $TG_N$ | 56 | 28 |
| $TG_N$ | 0 | 0 |
| $TG_N$ | 78 | 44 |
| $TG_N$ | 57 | 46 |
| $TG_N$ | 0 | 0 |
| $TG_N$ | 51 | 24 |
| $TG_N$ | 53 | 38 |
| $TG_N$ | 57 | 42 |
| $TG_N$ | 79 | 27 |
| Control (n = 12) | 0 | 0 |

TABLE 3

Characteristics of VEP response in $TG_N$-treated injured and intact nerves. The mean latency and amplitude of the first negative peak of activity are presented. ANOVA, one-factor analysis yielded.

| Group | Latency* (msec) (mean ± SE) | Amplitude** (μV) (mean ± SE) | Number of animals |
|---|---|---|---|
| $TG_N$-treated injured nerve | 61.6 ± 4.5 | 35.6 ± 3.4 | 7 |
| Intact nerve | 39.7 ± 1.4 | 131.8 ± 8.7 | 13 |

*DF = 1, F = 34.018, P = 0.0001.
** DF = 1, F = 93.101, P = 0.0001. Comparison according to Fisher revealed significance at 95%.

This experiment demonstrates recovery of function in adult transected mammalian CNS nerves after treatment that presumably facilitates growth within their own degenerative environment (Lavie et al., 1990). Other studies have achieved growth of CNS axons within their own environment, so far without physiological recovery. Thus, for example, it was shown that the use of hybridoma cells producing antibodies against myelin-associated inhibitors of mammals promotes regrowth within the spinal cord (Schnell and Schwab, 1990). Likewise, Millipore implants coated with embryonic astrocytes promoted growth of crushed dorsal root axons into the grey matter of the adult mammalian spinal cord (Rudge et al., 1990). Physiological activity of newly growing mammalian axons has been demonstrated, not as a result of a growth within the nerve's own environment, but after the nerve's own growth-hostile environment was replaced by an implanted peripheral nerve bridge; this resulted in a growth of axons along the length of the implant, all the way to the brain. Superior colliculus synapses were found but the axons penetrated only to a limited distance within the target CNS tissue (Kirstead et al., 1990; Aguayo et al., 1990a and 1990b).

In this experiment, functional recovery followed local application of the $TG_N$ enzyme, which is elevated after injury in a spontaneously regenerating nervous system. This enzyme, which was isolated from regenerating fish optic nerves, dimerizes IL-2 in vitro, thus altering its properties in such a way as to render it cytotoxic to oligodendrocytes. In the present experiment, $TG_N$ was applied in vivo, on the assumption that the active IL-2 dimer is formed in vivo, and that elimination of mature oligodendrocytes by the enzymatically-produced dimeric IL-2 soon after injury, at least in the immediate vicinity of the injury site, might facilitate growth, but other mechanisms of activity of the enzyme $TG_N$ should not be eliminated.

The VEP response is an objective physiological parameter indicative of the integrity of the visual system from the retina to the. cortex. In view of our finding that no VEP activity was detectable 1 week after injury but significant activity was recorded 5 weeks later, it is reasonable to assume that the VEP response is the result of axonal growth and reconnection. Moreover, in most of the $TG_N$-treated nerves the latency was prolonged relative to intact nerves, further supporting the notion that the response might be the result of newly growing (unmyelinated) axons which reinnervate the target.

Example 8
Preparation of linear dimeric IL-2

A linear dimeric IL-2 protein was constructed by the use of a viral expression vector, thus enabling large amounts of the linear IL-2 dimer to be expressed in the medium of the infected cells.

In this example, the following experimental procedures were used.

8.1 Lymphocytes and RNA preparation

Human lymphocytes were isolated and stimulated to maximize the amount of IL-2 mRNA. Peripheral venous blood was collected in 60-ml heparinized syringes and diluted with an equal volume of phosphate-buffered saline (PBS). The mixture was then layered on top of a 1.077 g/ml Percoll solution (49.2% Percoll, 150 mM NaCl) and centrifuged at 400×g for 25 min at 4° C. Lymphocyte-rich buffy coats were collected with a glass Pasteur pipette and washed twice in PBS. Lymphocytes were plated at $2\times10^6$ cells/ml and incubated for 3 days in the presence of 1 μg/ml peanut hemagglutinin (PHA; Sigma) in complete medium consisting of RPMI-1640 (Gibco), 2% heat-inactivated fetal calf serum (IFCS), 100 U/ml penicillin and 0.1 mg/ml streptomycin (Sigma), and $5\times10^{-5}$ M β-mercaptoethanol. Cells were then washed and plated onto new flasks at $2\times10^6$ cells/ml in complete medium and stimulated with 1 μg/ml PHA and 10 ng/ml phorbol 12-myristate 13-acetate (PMA) for 3 hr. Total cellular RNA was isolated by the RNAzol B method (Chomczynski and Sacchi, 1987) with the aid of the Biotec Laboratories kit, and quantified by absorbance at 260/280 nm.

8.2 Polymerase chain reaction (PCR) and sequence analysis

PCRs were carried out with the aid of the GeneAmp kit (Cetus, U.S.A.). Total human lymphocyte RNA (1 μg) was subjected to a reverse transcriptase reaction at 42° C. for 15 min with PCR buffer (1×, final), 5 mM $MgCl_2$, 1 U/μl RNase inhibitor, 50 pmol specific downstream primer and 1 mM of each dNTP in a total reaction volume of 20 μl. Following heat inactivation of the reverse transcriptase, the reaction mixture was made up to 100 μl by the addition of 50 pmol downstream primer, 100 pmol upstream primer, PCR buffer (1×, final), 2 mM $MgCl_2$ solution and 2.5 U taq DNA polymerase. The first PCR cycle was carried out for 1 min at 45° C., 1 min at 72° C., and 1 min at 94° C. This was followed by 30 cycles each of 30 sec at 55° C., 1 min at 72° C. and 1 min at 94° C. An extra 5 min at 72° C. was added at the end of the 30 cycles to ensure that the ends of the cDNAs were completely filled in, thus promoting proper digestion with restriction enzymes (if reactions were started from an amplified DNA, each of 30 cycles lasted for 1 min at 94° C. and 1.5 min at 72° C., so that nonspecific amplified bands could be eliminated). The PCR products were ligated to an appropriately digested bluescript KS-vector. Each of the DNAs to be ligated (10 ng) was heated to 65° C. for 5 min, and then incubated for 15 min at room temperature with ligation buffer (1×, final; Stratagene) and 5 U of T4 DNA ligase (Stratagene) in a total reaction volume of 10 μl. Ligation took place during overnight incubation at 15° C. The recombinants were cloned (to *Epicurian coli,* Sure competent cells; Stratagene) and plated for overnight growth on plates containing ampicillin. Positive clones were defined according to the alkali method for miniscale DNA preparations (Sambrook et al., 1989), followed by restriction enzyme analysis and gel electrophoresis. Positive clones were sequenced by the Sanger dideoxy chain termination technique with the aid of the Sequenase kit (USB).

8.3 Transfection of cells, generation of viral vector and protein extraction

Rabbit skin (RS) cells and African green monkey kidney (Vero) cells were grown in Dulbecco's modified Eagle's medium (DMEM) supplemented with 10% IFCS, 1% glutamine, and 1% penicillin-streptomycin. RS cells were transfected with 20 μg of pCB-IL-2 dimer (described hereinafter) by the calcium phosphate method (Graham and van der Eb, 1973) with subsequent glycerol shock (Parker and Stark, 1979). Transfection efficiencies, ranging between 10 and 20%, were determined on the basis of the number of blue cells/total cells per plate, by histochemical detection of bacterial β-galactosidase (Sanes et al., 1986), in cells cotransfected with 10 μg of the pCB-IL-2 dimer and 10 μg of x-gal plasmid DNA. Following overnight incubation at 37° C. and 5% $CO_2$, the medium was removed and cells were superinfected with the temperature-sensitive HSV1 (Graham and van der Eb, 1973) tsK strain (Davison et al., 1984), at a multiplicity of infection (moi) of 0.1 plaque-forming units (pfu)/cells. Following incubation for 1.5 hr at 31.5° C., cells were washed twice with PBS supplemented with 1% IFCS and incubated at the same temperature in DMEM/1% IFCS/1% penicillin-streptomycin/1% glutamine.

Viral stocks were harvested when all of the cells exhibited a cytopathic effect, usually 2 days after superinfection.

Rounded cells in the medium were pelleted at 1000 g for 5 min, and the pellets were resuspended in 1 ml of virus buffer (150 mM NaCl/20 mM Tris, pH 7.5). Suspensions were rapidly frozen at −70° C. and thawed to 37° C. (repeated three times), and were then used to infect Vero cells at different dilutions of the defective virus. Following overnight incubation at 37° C. (a nonpermissive temperature for tsK), the medium containing the released synthesized protein was collected and the cells were extracted by incubation for 2 hr at 4° C. in 10 mM Tris, pH 7.5, 150 mM NaCl, 1% Triton, 1 mM EDTA, 1 mM spermidine, and protease inhibitors (25 μg/ml leupeptine and 5 μg/ml pepstatin), after which the supernatants were collected. The resulting products were subjected to Western blot analysis (Eitan et al., 1992) to verify the expression of IL-2 dimeric protein in the medium/extracts of the infected cells.

8.4 Construction of human IL-2 cDNA products by PCR

Figure 9B:
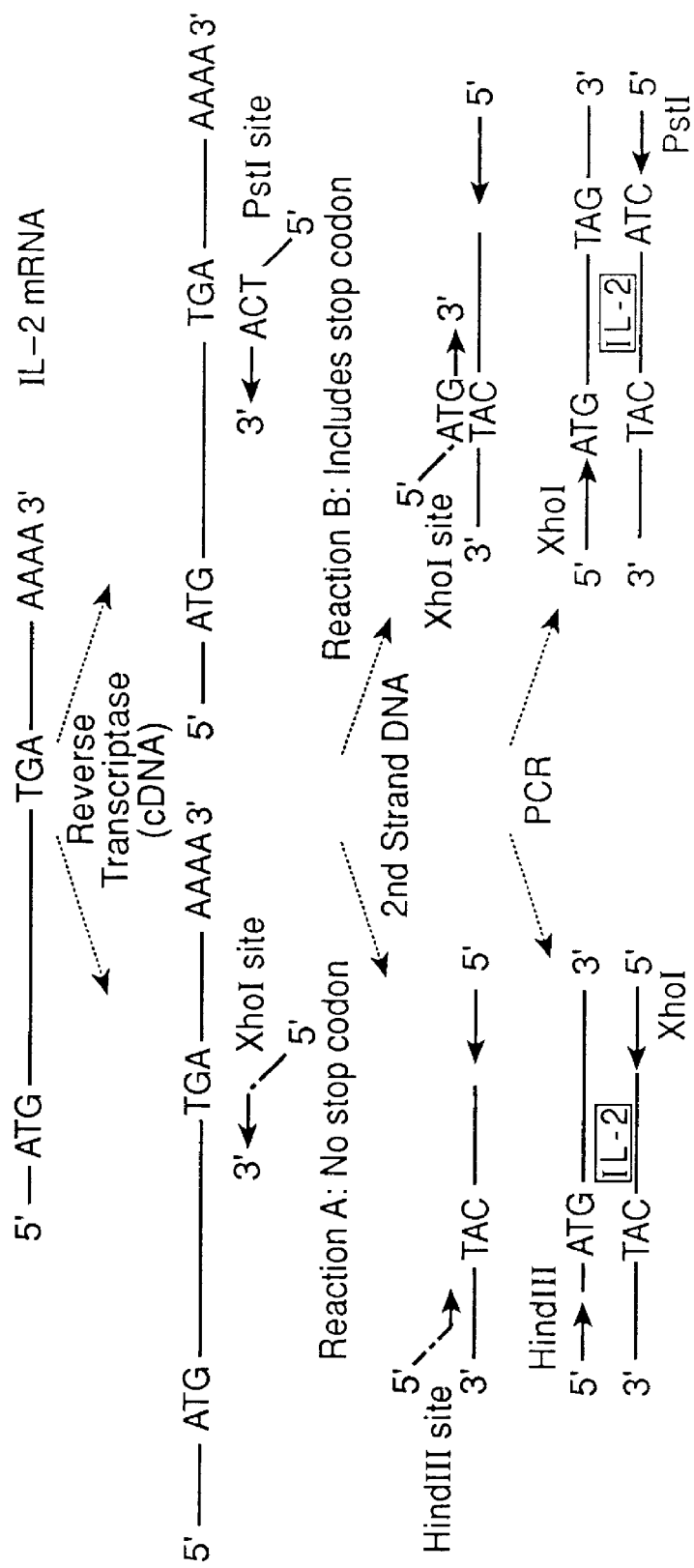

The IL-2 cDNA sequence derived from human lymphocytes (Taniguchi et al., 1983) was run through a primer designer program which assists in the choice of optimal primers for PCR. In parallel, the sequence was run through a clone manager program, which yielded a restriction map that allowed us to detect restriction sites not present in the IL-2 gene. These sites were added to the ends of the primers. We then ran two PCRs: reaction A produced a copy of the IL-2 cDNA that included all translated codons, but stopped immediately before the last translated codon, so that there was no stop codon; the product of reaction B started with the first translated codon but ended beyond the stop site, so that the stop codon was included. The two sets of primers and PCRs are illustrated in FIG. 9. The restriction sites engineered on the downstream primer for reaction A and the upstream primer for reaction B were the same, thus allowing the construction of a dimerized cDNA by fusion of the products of A and B in frame and in the appropriate orientation. Since a restriction site was added, there were six bases between the last codon of product A and the first codon of product B, which resulted in the addition of two amino acids at the junction. We anticipated that the contribution of the two extra amino acids to each of the IL-2 monomeric molecules in the dimer would be minimal.

8.5 Sequence analysis of the PCR products

Since the PCR products were used in expression experiments, it was important to verify that no mutations had been introduced during the PCR process. Three positive appropriately digested clones (as described in 8.2 above) of each PCR type were chosen for sequence analysis in which one of each set of clones was found to express the right sequence, with no mutations. These two clones were chosen for construction of the linear IL-2 dimer.

8.6 Construction of the linear IL-2 dimer in the defective viral vector

Figure 10:
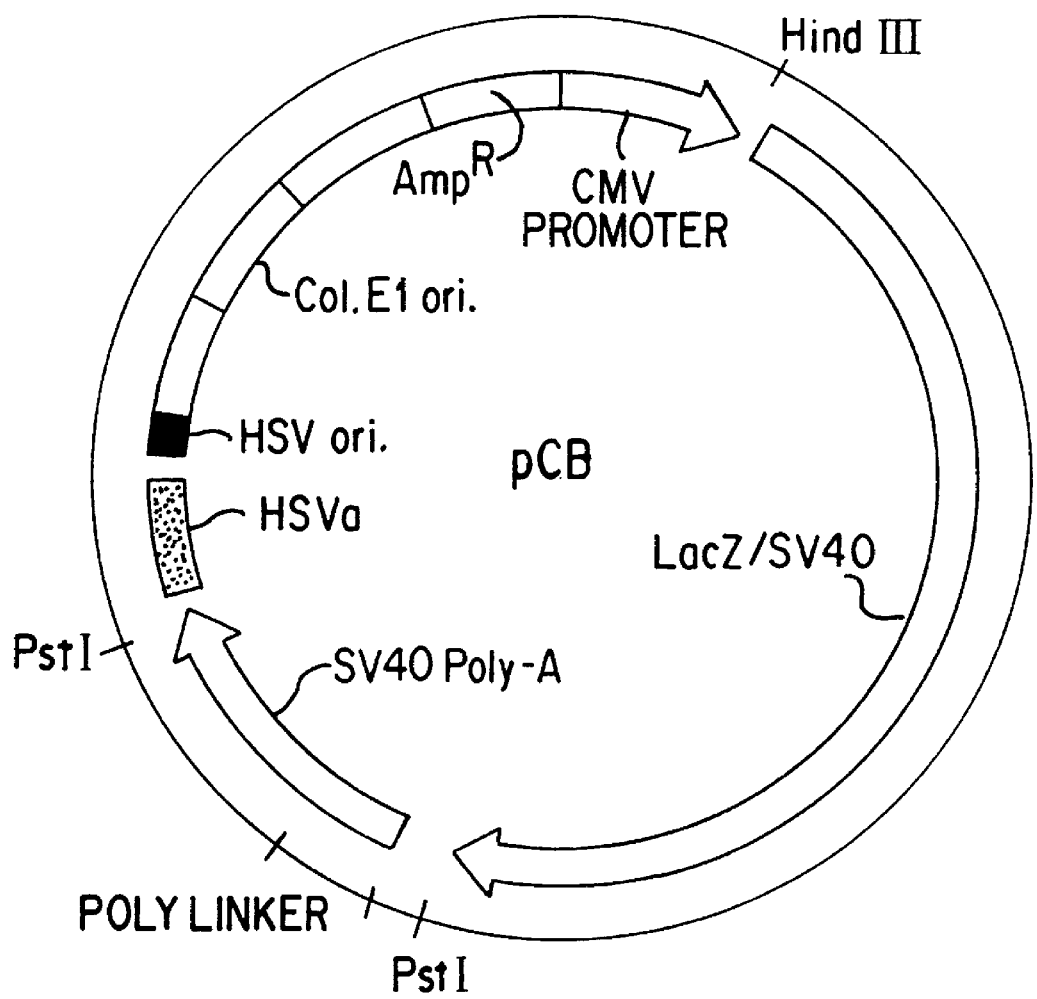
FIG. 10 depicts the defective viral vector amplicon plasmid pCB. The amplicon includes a fragment from pRB3119 containing the HSV1 cleavage/packaging signal (HSVa), a fragment containing an HSV origin of DNA replication (HSV ori), and a fragment from pcDNAlac containing the CMV promoter, lacZ gene, and simian virus 40 polyadenylation signal [poly(A)+signal]. These sequences were inserted into the ampicillin-resistant plasmid pT7-3, containing a β-lactamase gene (Amp$^R$) and a bacterial origin of DNA replication (Col El ori). This amplicon served as the basis for the defective viral vector genome used in the application.

The prototype of the defective viral vector used herein (pCB; FIG. 10) includes a fragment from pRB3119 containing the HSV1 cleavage/packaging signal (HSVa), a fragment containing an HSV origin of DNA replication (HSV ori), and a fragment from pcDNAlac containing the cytomegalovirus (CMV) promoter, lacz gene, and simian virus 40 polyadenylation signal [poly(A)+signal]. These sequences were inserted into the ampicillin-resistant plasmid pT7-3, which contains a β-lactamase gene (Amp$^R$) and a bacterial origin of DNA replication (Col El ori). As a first step, the lacZ gene was cut out of the vector. This was done by linearization of the vector with HindIII, followed by its partial digestion with PstI and extraction of the right vector band from an agarose gel with the aid of the Geneclean II kit (BIO 101). The two PCR products were ligated, in a triple ligation, into the resulting vector (their correct direction, A followed by B, was determined by the previously designed complementary restriction sites of the two products, as discussed in 8.4 above). The resulting construct, pCB-IL-2 dimer, was double-checked by restriction enzyme analysis, followed by large-scale DNA preparation (CsCl) (Sambrook et al., 1989), and transfected into the rabbit skin (RS) cells. Harvested viral stocks were used to infect African green monkey kidney (Vero) cells, as discussed in 8.3 above.

Example 9

Analysis of the linear dimeric IL-2 protein product

Figure 11A:
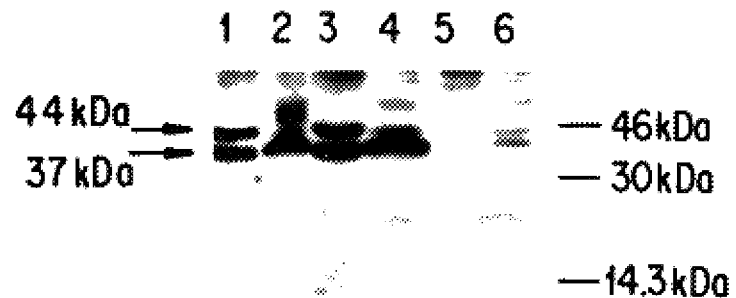
FIG. 11A–B show Western blot analysis of the linear IL-2 dimer with mouse antihuman IL-2 monoclonal antibodies.
Figure 11B:
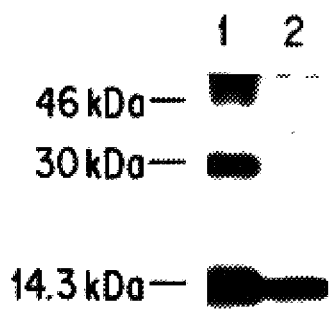

Since IL-2 protein is known to be released into the medium of growing cells, the medium of the infected Vero cells obtained in Example 8.6 above was collected and used as a source of the linear dimeric IL-2 protein. In parallel, cell extracts were prepared and examined under the same conditions in order to determine whether the synthetic protein was retained in the infected cells. The two suspensions were subjected to Western blot analysis by the use of monoclonal antibodies directed against human IL-2 (FIG. 11, left panel). Two dilutions (1:3, lanes 1,3,5, and 1:9, lanes 2,4,6) of cell supernatants (lanes 1,3) and extracts (lanes 2,4), and of supernatant (lane 5) and cell extract (lane 6), obtained from cells infected by the defective virus only, were analyzed. In contrast to the cells infected only with the defective virus (lanes 5,6), where no IL-2 immunoreactive band could be detected, all four lanes (1–4) containing either supernatants (1,3) or cell extracts (2,4) expressed bands of about 37 kd that immunoreacted with the specific IL-2 monoclonal antibodies. The commercial human monomeric IL-2 protein has a molecular weight of 14 kd and the dimeric protein synthesized from the commercial monomeric IL-2 by the nerve-derived transglutaminase as described hereinbefore, has a molecular weight of 28 kd (FIG. 11, right panel, lanes 2 and 1, respectively). The difference in size between the dimeric IL-2 produced by the two different procedures may be explained by posttranslational modifications of the linear dimerized protein in the infected cells, in contrast to the dimer synthesized in vitro by transglutaminase and monomeric IL-2. The supernatants (lanes 1,3) contained an extra band of about 44 kd. This extra band can also be explained in terms of posttranslational modifications, such as glycosylation or phosphorylation, which may have occurred during the release of the protein into the medium.

Example 10

Linear dimeric IL-2 is not cytotoxic to oligodendrocytes

We then attempted to find out whether this linear human IL-2 dimer could mimic the transglutaminase-dimerized human IL-2 of the invention with respect to in vitro cytotoxicity. To investigate this possibility, aliquots from the same samples and the same dilutions of the supernatants as those used in Example 9 for Western blot analysis were applied to cultures of rat oligodendrocytes.

Figure 12:
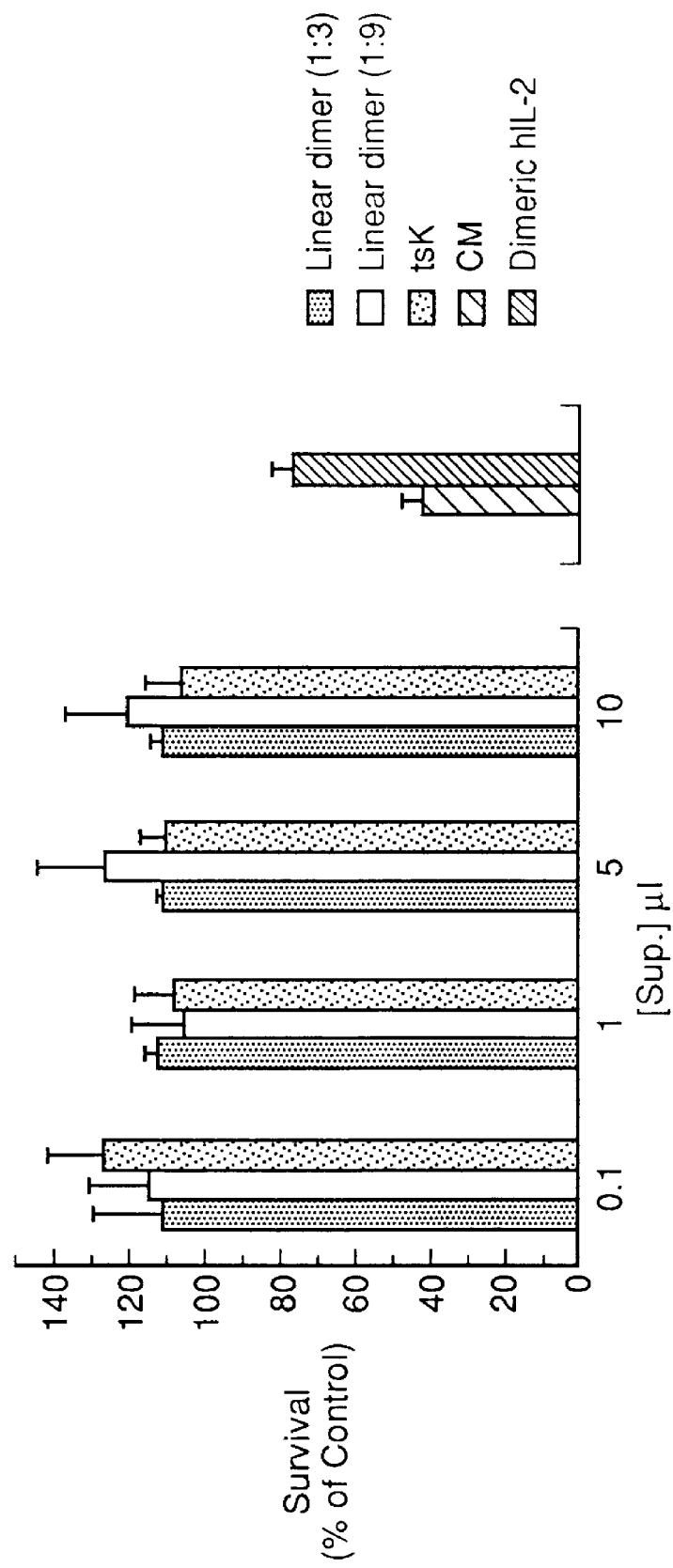

Enriched oligodendrocyte cultures derived from neonatal rat brain were prepared as described (Bottenstein and Sato, 1979 and seeded on glass coverslips previously coated with poly-L-lysine (PLL)(Eitan et al. 1992). After 48 hr, the seeded cells were treated with the aliquots of the linear dimeric IL-2 protein and the extent of cytotoxicity was determined by the number of surviving cells assessed calorimetrically (Eitan et al.,1992). The numbers of mature oligodendrocytes, asssayed by the calorimetric method, were not reduced relative to untreated cells used as control (100%) in any of the dilutions of the linear dimer or tsK used as a control (FIG. 12, left panel). No reduction could be detected even at high protein concentrations (FIG. 12, left panel). On the other hand, soluble substances derived from regenerating fish optic nerves in which the IL-2-like cytotoxic factor was identified (Eitan et al., 1992), as well as human dimeric IL-2 enzymatically synthesized in vitro, caused significant reductions in the numbers of mature oligodendrocytes (FIG. 12, right panel).

Example 11

Figure 13:
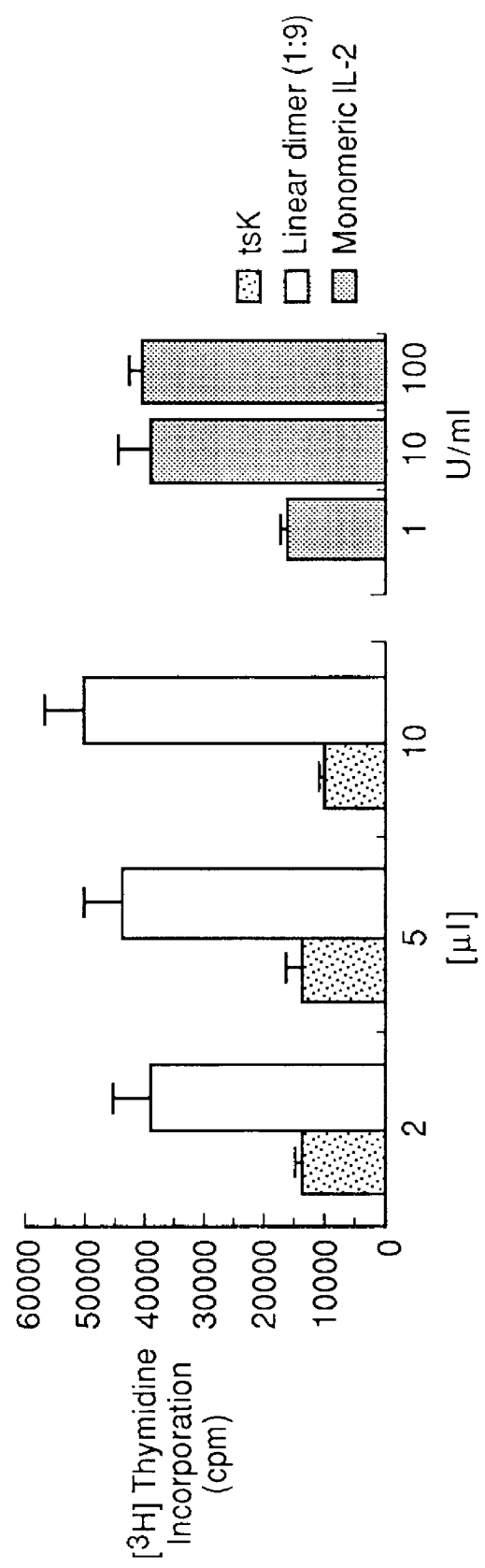

Detection of IL-2 biological activity in the linear dimeric IL-2 using an IL-2-dependent T cell line To exclude the possibility that lack of cytotoxicity of the linear dimer on oligodendrocytes is not caused by loss of activity of the IL-2 protein as a result of expression via the HSV1 vector, we assayed the activity of the linear dimer and assessed its ability to mimic the monomeric Il-2 as a mitogen on T cell line (CTLL-2). Thus CTLL-2 cells were seeded in multiwell culture plates ($2 \times 10^3$ cells/100 µl of RPMI containing 10% IFCS, 2 mM glutamine and 0.05 mM β-mercaptoethanol). After 2–3 hr, aliquots from the same samples and the same dilution (1:9) of the supernatant as those used for Western blot analysis and for the cytotoxicity assay were applied to the cells for an overnight incubation at 37° C. One µCi of [$^3$H] thymidine was added to each well, for an additional 4-h incubation. At the end of the incubation, cells were harvested and thymidine incorporation was detected by cpm. Measurement of thymidine incorporation (cpm) showed that, in contrast to tsK used as a control, the addition of different concentrations of the linear dimer caused cell proliferation in a dose-dependent manner (FIG. 13, left panel). The observed proliferation was even higher than that caused by the commercial monomeric IL-2 used as a control (FIG. 13, right panel).

This experiment shows that the resulting linear dimeric IL-2, being a translational product, differs from the enzymatically produced dimer, which is a posttranslational modification of IL-2, with respect to citotoxicity to oligodendrocytes. The linear dimer, while retaining the known IL-2 activity of monomeric IL-2 with respect to mitogenicity on T cells, was not cytotoxic to oligodendrocytes, suggesting that the lack of oligodendrocyte cytotoxicity of the linear dimeric IL-2 is not caused by a loss of biological activity during its preparation, but is related to its conformational structure, which evidently does not meet the requirements for oligodendrocyte cytotoxicity.

REFERENCES

Aguayo, A. J., G. M. Bray, M. Rasminsky, T. Zwimpfer, D. A. Carter and M. Vidal-Sanz (1990a) J. Exp. Biol. 153:199.

Aguayo, A. J., G. M. Bray, D. A. Carter, M. P. Villegas-Perez, M. Vidal-Sanz and M. Rasminsky (1990b) Acta Neurobiol. Exp. 50:381.

Bottenstein, J. E. and G. H. Sato (1979) Proc. Natl. Acad. Sci. U.S.A. 76:514–517.

Chakrabarty, G. et al.(1987) J. Neurochem. 48:669.

Chomczynski, P., and N. Sacchi (1987) Anal. Biochem. 162:156–159.

Cohen, A., T. Sivron, R. Duvdevani and M. Schwartz (1990) Brain Res. 537:24–32.

Davison, M. J., V. G. Preston and D. J. McGeoch (1984) J. Gen. Virol. 65:859–863.

Devos, R. (1983) Nucleic Acids Research 11:4307–4323.

Eitan, S., R. Zisling, A. Cohen, M. Belkin, D. L. Hirschberg, M. Lotan and M. Schwartz (1992) Proc. Natl. Acad. Sci. U.S.A. 89:5442–5446.

Graham, F. L. and A. J. van der Eb (1973) Virology 52:456–467.

Greenberg, C. S., P. J. Birckbichler and R. H. Rice (1991) FASEB J. 5:3071.

Kierstead, S. A., M. Rasminsky, J. Fukuda, D. A. Carter, A. J. Aguayo and M. Vidal-Sanz (1990) Science 246:255.

Lavie, V., M. Murray, A. Solomon, S. Ben-Bassat, S. Rumelt, M. Belkin and M. Schwartz (1990) J. Comp. Neurol. 298:293–314.

Parker, B. A. and G. R. Stark (1979) J. Virol. 31:360–369.

Robb, R. J. et al. (1983), Proc. Natl. Acad. Sci. U.S.A. 80:5990.

Rudge, J. S. and J. Silver (1990) J. Neurosci. 10:3594.

Sanes, J. R., J. L. R. Rubenstein and J. F. Nicolas (1986) EMBO J. 5:3133–3142

T. Sivron. et al.(1991) Glia 4:591–601.

Schnell, L. and M. E. Schwab (1990) Nature 343:269.

Taniguchi, T., H. Matsui, T. Fujita, C. Takaoka, N. Kashima, R. Yoshimoto and J. Hamuro (1983) Nature 302:305–310.

We claim:

1. A purified nerve-derived transglutaminase enzyme obtainable from injured fish optic nerve which converts IL-2 to a dimeric IL-2 having oligodendrocyte cytotoxic activity.

2. A purified nerve-derived transglutaminase according to claim 1 having a molecular weight of about 55 kDa as determined by SDS-PAGE and silver staining.

3. A purified nerve-derived transglutaminase according to claim 1 which is detected at elevated levels in the fish optic nerve after injury, as compared with intact fish optic nerve.

4. A purified nerve-derived transglutaminase according to claim 1 which converts IL-2 to dimeric IL-2 having oligodendrocyte cytotoxic activity.

5. A purified nerve-derived transglutaminase according to claim 4, which converts mammalian IL-2 to dimeric IL-2 having oligodendrocyte cytotoxic activity.

6. A purified nerve-derived traneglutaminase according to claim 5 which converts murine recombinant IL-2 to dimeric IL-2 having oligodendrocyte cytotoxic activity.

7. A purified nerve-derived transglutaminase according to claim 5 which converts human recombinant IL-2 to dimeric IL-2 having oligodendrocyte cytotoxic activity.

8. A purified nerve-derived transglutaminase enzyme $TG_n$ having the following characteristics;

(i) it is water-soluble;

(ii) it is obtainable from regenerating fish optic nerve;

(iii) it converts immune IL-2 to dimeric IL-2 having oligodendrocyte cytotoxic activity;

(iv) it has a molecular weight of about 55 kDa as determined by SDS-PAGE and silver staining;

(v) it is detected at elevated levels in injured fish optic nerve as compared with intact fish optic nerve;

(vi) it incorporates putrescine to a carrier protein in the assay characteristic of the transglutaminase family;

(vii) it is optimally active in the incorporation of putrescine at pH 9 and at 56° C.;

(viii) its $K_m$ in the incorporation of putrescine is $5.5 \times 10^{-7}$ calculated as a function of substrate;

(ix) it is a $Ca^{2+}$-dependent enzyme as regards the IL-2 dimerization process; and (x) it shows an immunoreactive band in Western blot analysis with antibodies raised against peptides corresponding to two sites of transglutaminases, said peptides being selected from a 14-mer peptide corresponding to the active site of transglutaminases, of the sequence:

Lys-Lys-Val-Lys-Tyr-Gly-Gln-Cys-TrP-Val-Phe-Ala-Gly-Val, and a 10-mer peptide of the sequence:

Asn-Ser-Lys-Leu-Thr-Lys-Lys-Lys-Lys-Lys-.

9. A purified nerve-derived transglutaminase according to claim 8, which converts mammalian IL-2 to dimeric Il-2 having oligodendrocyte cytotoxic activity.

10. A purified nerve-derived transglutaminase according to claim 8 which converts murine recombinant IL-2 to dimeric IL-2 having oligodendrocyte cytotoxic activity.

11. A purified nerve-derived transglutaminase according to claim 8 which converts human recombinant IL-2 to dimeric IL-2 having oligodendrocyte cytotoxic activity.

12. A pharmaceutical composition for treating injured nerves of the central nervous system of a mammal comprising an effective amount of the purified nerve-derived transglutaminase of claim 1.

13. A pharmaceutical composition for treating injured nerves of the central nervous system of a mammal comprising an effective amount of the purified nerve-derived transglutaminase of claim 8.

* * * * *